(12) United States Patent
Nakanishi et al.

(10) Patent No.: US 7,858,244 B2
(45) Date of Patent: Dec. 28, 2010

(54) FUEL CELL AND METHOD FOR MANUFACTURING FUEL CELL

(75) Inventors: Haruyuki Nakanishi, Susono (JP); Yusuke Kuzushima, Kyoto (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 12/310,991

(22) PCT Filed: May 21, 2008

(86) PCT No.: PCT/IB2008/001260

§ 371 (c)(1), (2), (4) Date: Mar. 16, 2009

(87) PCT Pub. No.: WO2008/142532

PCT Pub. Date: Nov. 27, 2008

(65) Prior Publication Data

US 2010/0055526 A1 Mar. 4, 2010

(30) Foreign Application Priority Data

May 21, 2007 (JP) .............................. 2007-133997

(51) Int. Cl.
*H01M 8/18* (2006.01)
(52) U.S. Cl. ..................................... 429/401; 429/417

(58) Field of Classification Search ................. 429/401, 429/417, 405, 407, 425, 408, 423, 424
See application file for complete search history.

(56) References Cited

U.S. PATENT DOCUMENTS

2004/0101741 A1* 5/2004 Minteer et al. ................ 429/43
2007/0077483 A1 4/2007 Kubo et al.

FOREIGN PATENT DOCUMENTS

| JP | A-2002-270209 | 9/2002 |
| JP | A-2004-71559 | 3/2004 |
| JP | A-2005-310613 | 11/2005 |
| JP | A-2006-508519 | 3/2006 |
| WO | WO 2004/051774 A2 | 6/2004 |
| WO | WO 2005/096430 A1 | 10/2005 |

OTHER PUBLICATIONS

Varcoe et al., "Prospects for Alkaline Anion-Exchange Membranes in Low Temperature Fuel Cells," *Fuel Cells*, vol. 5, No. 2, 2005, pp. 187-200.

* cited by examiner

*Primary Examiner*—Jennifer Michener
*Assistant Examiner*—Monqiue Wills
(74) *Attorney, Agent, or Firm*—Oliff & Berridge, PLC

(57) ABSTRACT

A fuel cell that uses alcohol as a fuel and including an electrolyte, and an anode and a cathode that are disposed across the electrolyte. The anode of the fuel cell contains a first particle that catalyzes the degradation of alcohol, and a second particle that catalyzes the degradation of aldehyde.

10 Claims, 5 Drawing Sheets

F I G . 2
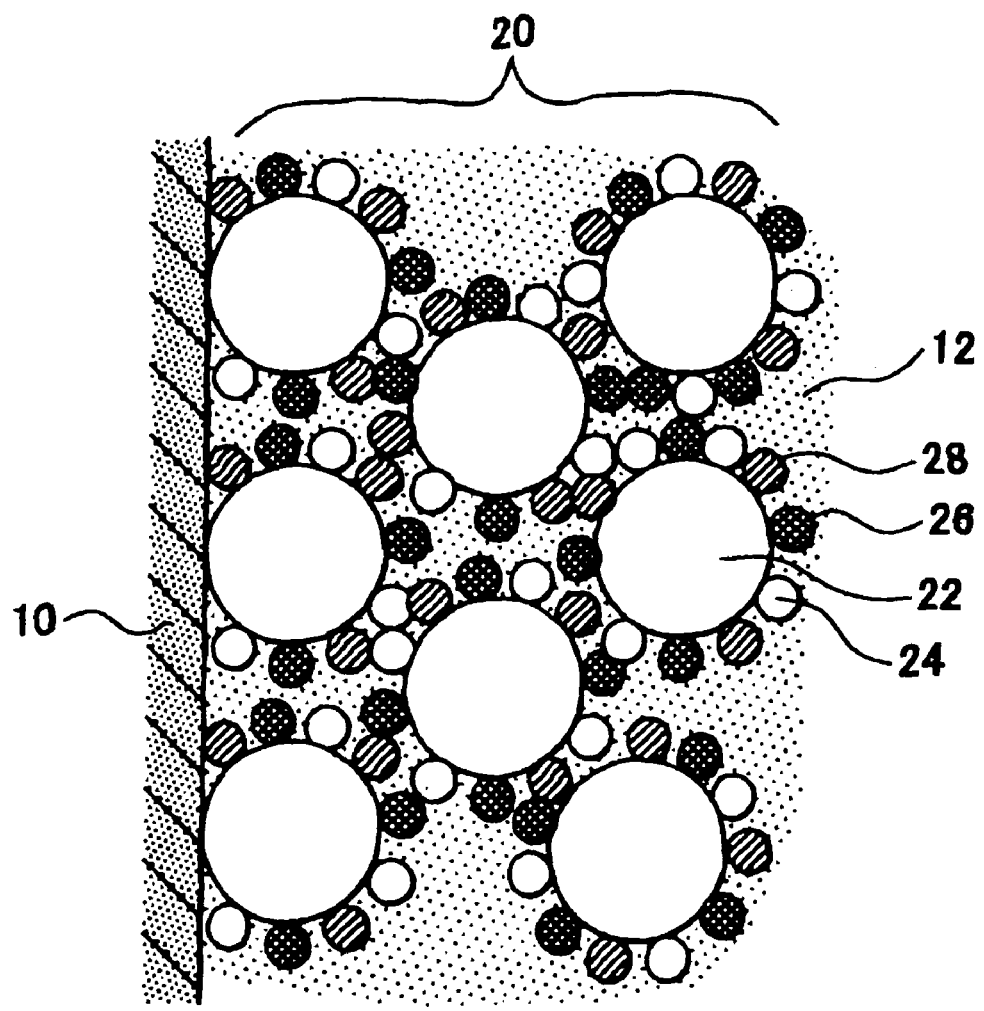

I-V CHARACTERISTICS MEASURED USING
ENZYMATIC CATALYST-CARRYING MEA

RATIOS BETWEEN ALCOHOL DEGRADING ENZYME AND
ALDEHYDE DEGRADING ENZYME AND CURRENT DENSITY AT 0.6V

| ALCOHOL DEGRADING ENZYME (%) | 20 | 40 | 60 | 80 |
|---|---|---|---|---|
| ALDEHYDE DEGRADING ENZYME (%) | 80 | 60 | 40 | 20 |
| CURRENT DENSITY (A/cm$^2$) | 0.029 | 0.042 | 0.022 | 0.009 |

FUEL CELL AND METHOD FOR MANUFACTURING FUEL CELL

BACKGROUND OF THE INVENTION

1. Field of the Invention

The present invention relates to a fuel cell. More specifically, the present invention relates to a fuel cell that uses alcohol as fuel and a method for manufacturing such a fuel cell.

2. Description of the Related Art

Japanese Patent Application Publication No. 2002-270209 (JP-A-2002-270209), for example, describes a polymer electrolyte fuel cell having an anode configured to be advantageous when a fuel other than hydrogen is used. Specifically, a layer containing a biochemical catalyst is formed over the surface of the anode of the fuel cell. The biochemical catalyst layer catalyzes the degradation of the raw materials of the fuel to generate hydrogen.

That is, if methanol is used as the fuel, for example, the methanol is degraded as it passes through the biochemical catalyst layer. At this time, hydrogen is produced in the biochemical catalyst layer. The hydrogen is supplied to the anode at the inner side (at the side of an electrolyte film) to generate protons and electrons. Thus, according to the above related art, pure hydrogen is supplied to the anode even when an alcohol, such as methanol, is used as the fuel, and therefore it is possible to reduce poisoning of the anode by carbon compounds contained in the fuel.

If the fuel cell uses a fuel other than pure hydrogen, such as alcohol, for example, the proportion of hydrogen contained in the fuel is low. Therefore, in order to improve the power generation performance of the fuel cell using a fuel other than pure hydrogen, it is important to efficiently degrade the fuel and generate hydrogen. For this purpose, in the related art described in JP-A-2002-270209, Japanese Patent Application Publication No. 2004-71559 (JP-A-2004-71559), and Published Japanese Translation of PCT Application No. 2006-508519 (JP-A-2006-508519), poisoning of the anode is reduced by supplying pure hydrogen generated in the biochemical catalyst layer to the anode at the inner side. In the described fuel cells, however, the efficiency and rate of the reaction to generate hydrogen in the biochemical catalyst layer are not taken into account. In order to improve the power generation performance of the fuel cell by improving the utilization efficiency of fuel, it has been expected to develop an electrode that can generate hydrogen from the fuel at a higher efficiency.

SUMMARY OF THE INVENTION

The present invention provides a fuel cell that uses alcohol as fuel with its power generation performance improved by improving the utilization efficiency of the fuel, and a method for manufacturing such a fuel cell.

A first aspect of the present invention is directed to a fuel cell that uses alcohol as fuel. The fuel cell includes: an electrolyte; an anode and cathode pair that is disposed across the electrolyte, and the anode contains a first particle that catalyzes the degradation of alcohol, and a second particle that catalyzes the degradation of aldehyde.

According to the above configuration, even if the fuel cell uses alcohol as fuel, the first particle and the second particle degrade the alcohol in two stages, which increases the yield of hydrogen. Thus, it is possible to utilize the fuel with higher efficiency, and to improve the power generation performance of the fuel cell.

In the fuel cell in accordance with the above aspect, the first particle may contain alcohol dehydrogenase.

By utilizing alcohol dehydrogenase, it is possible to degrade the fuel more reliably and rapidly, and to improve the utilization efficiency of the fuel and the power generation performance of the fuel cell.

In the fuel cell in accordance with the above aspect, the first particle may contain at least one of Fe, Co, Ni, Fe—Co—Ni, Pt, Pt—Ru, and Pt—Sn. In particular, the first particle may contain a particle consisting of Pt—RuPt—Ru.

By utilizing such a particle, hydrogen can be reliably generated from the fuel.

In the fuel cell in accordance with the above aspect, the second particle may contain acetaldehyde dehydrogenase.

This makes it possible to generate hydrogen by further degrading the aldehyde produced during the course of alcohol degradation. Thus, it is possible to enhance the utilization efficiency of the fuel, and to improve the power generation performance of the fuel cell.

In the fuel cell in accordance with the above aspect, the first particle and the second particle both may contain cytochrome P450.

The inclusion of cytochrome P450 at the anode makes it possible to efficiently degrade the alcohol and generate hydrogen. The cytochrome P450 improves the hydrogen generation efficiency by directly degrading alcohol into carbon dioxide and water. Thus, it is possible to enhance the utilization efficiency of the fuel, and to improve the power generation performance of the fuel cell.

In the fuel cell in accordance with the above aspect, the anode may include a carrying body in which the first particle and the second particle are both carried on the same carrier.

This increases the rates of the reaction to degrade the alcohol and the subsequent reaction to degrade the aldehyde by providing the first particle and the second particle close to each other. Thus, it is possible to enhance the utilization efficiency of the alcohol fuel, and to improve the power generation performance of the fuel cell.

In the fuel cell in accordance with the above aspect, the first particle may contain an alcohol dehydrogenase; the second particle may contain an acetaldehyde dehydrogenase; and the molar ratio of the alcohol dehydrogenase to the acetaldehyde dehydrogenase may be 0.25 to 4, more particularly 0.25 to 1.5.

In the fuel cell in accordance with the above aspect, the electrolyte may be an anion exchange membrane.

A second aspect of the present invention is directed to a method for manufacturing a fuel cell that uses alcohol as fuel and that has an anion exchange membrane as an electrolyte. This manufacturing method includes: mixing a first solution that contains alcohol dehydrogenase and a second solution that contains acetaldehyde dehydrogenase; drying a mixed solution obtained by mixing the first solution and the second solution; dissolving an anion exchange membrane in a solution to form an electrolyte solution; mixing a dried substance obtained by drying the mixed solution with the electrolyte solution; and applying the electrolyte solution, mixed with the dried substance, to the anion exchange membrane.

In the method for manufacturing a fuel cell in accordance with the above aspect, the molar ratio of the alcohol dehydrogenase to the acetaldehyde dehydrogenase contained in the mixed solution may be 0.25 to 4.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein:

FIG. 2 is a diagram illustrating an electrode catalyst of the fuel cell in accordance with the embodiment of the present invention;

DETAILED DESCRIPTION OF EMBODIMENTS

Figure 1:
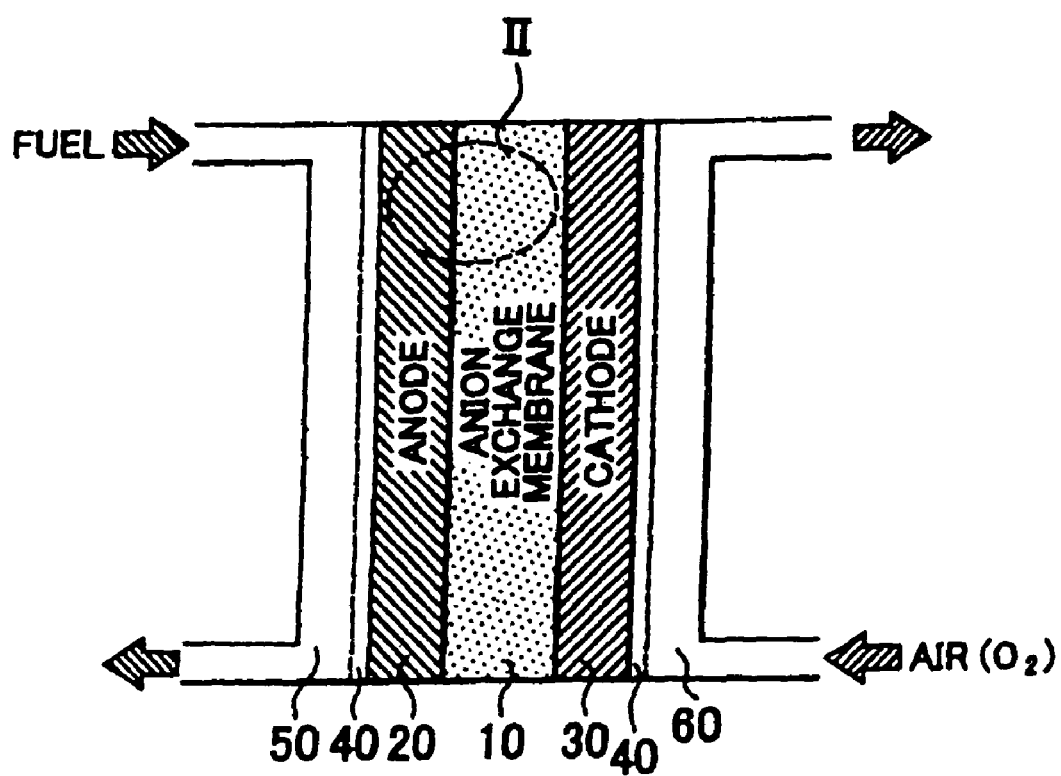
FIG. 1 is a schematic diagram illustrating a fuel cell in accordance with an embodiment of the present invention.

An embodiment of the present invention will hereinafter be described with reference to the drawings. In the drawings, same or corresponding parts are denoted by same or corresponding reference numerals to simplify or omit their descriptions.

FIG. 1 is a schematic diagram illustrating the configuration of a fuel cell in accordance with an embodiment of the present invention. The fuel cell shown in FIG. 1 is an alkali fuel cell. The fuel cell has an anion exchange membrane 10 (electrolyte). An anode 20 and a cathode 30 are disposed on opposite sides of the anion exchange membrane 10. Current collecting plates 40 are disposed on both outer sides of the anode 20 and the cathode 30. A fuel path 50 connected to a fuel supply source (not shown) is connected to the current collecting plate 40 on the anode 20 side. Fuel is supplied from the fuel supply source via the fuel path 50 and the anode-side current collecting plate 40 to the anode 20, from which unreacted fuel and so forth is discharged to the fuel path 50. An oxygen path 60 is connected to the cathode-side current collecting plate 40. Atmospheric air is supplied via the oxygen path 60 and the cathode-side current collecting plate 40 to the cathode 30, from which atmospheric off-gas containing unreacted oxygen is discharged to the oxygen path 60.

To generate electricity, a fuel having a carbon bond and containing hydrogen such as ethanol, for example, is supplied to the anode 20. When the fuel is supplied to the anode 20, the anode 20 causes hydrogen atoms in the fuel and hydroxide ions having passed through the anion exchange membrane 10 to react, which generates water and releases electrons. The reaction at the anode 20 is represented by the following formula (1) when pure hydrogen is supplied as fuel, and by formula (2) when ethanol is supplied as fuel.

$$H_2 + 2OH^- \rightarrow 2H_2O + 2e^- \quad (1)$$

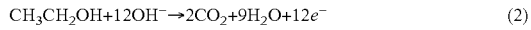

$$CH_3CH_2OH + 12OH^- \rightarrow 2CO_2 + 9H_2O + 12e^- \quad (2)$$

Atmospheric air (or oxygen) is supplied to the cathode 30. When atmospheric air is supplied to the cathode 30, the cathode 30 performs its catalytic function, for oxygen molecules in the atmospheric air to receive electrons from the electrode to generate hydroxide ions through several stages. The hydroxide ions pass through the anion exchange membrane 10 and move to the anode 20 side. The reaction at the cathode 30 is represented by formula (3).

$$1/2 O_2 + H_2O + 2e^- \rightarrow 2OH^- \quad (3)$$

Summarizing the reactions at the anode 20 and the cathode 30 described above, the reaction to generate water represented by the following formula (4) takes place in the fuel cell overall. During this reaction, electrons move via both the anode-side and cathode-side current collecting plates 40 as a current, thereby generating electricity.

$$H_2 + 1/2 O_2 \rightarrow H_2O \quad (4)$$

The anion exchange membrane 10 provided in the alkali fuel cell is not specifically limited, as long as the medium permits the movement of hydroxide ions (OH⁻), generated by the electrode catalyst of the cathode 30, to the anode 20. Specific examples of the anion exchange membrane 10 include solid polymer membranes (anion exchange resins) having an anion exchange group such as primary to tertiary amino groups, a quaternary ammonium group, a pyridyl group, an imidazole group, a quaternary pyridinium group, and a quaternary imidazolium group. Suitable solid polymer membranes include hydrocarbon-based resins and fluorine-based resins.

The configuration of the cathode 30 is not specifically limited, as long as it catalyzes the reaction to generate hydroxide ions from the supplied atmospheric air. Examples of the material composing the catalyst of the cathode 30 include a material containing metal such as iron (Fe), platinum (Pt), cobalt (Co), and nickel (Ni), a material in which one or more of these metals are carried on a carrier such as carbon, an organometallic complex having atoms of these metals as its central metal, and a material in which these organometallic complexes are carried on a carrier. The surface of the catalyst may be covered by a diffusion layer composed of a porous material or the like.

The anode 20 is required to have a catalytic function of generating hydrogen from the fuel supplied and causing the hydrogen to react with the hydroxide ions to generate water. When an alcohol is used as the fuel, it is important to efficiently generate a large amount of hydrogen from alcohol in order to improve the fuel utilization efficiency of the fuel cell.

It is known that alcohol taken into an organism is degraded by the action of enzymes into carbon dioxide and water, before being discharged from the organism. Specifically, an alcohol such as ethanol ($CH_3CH_2OH$) is first oxidized by alcohol dehydrogenase (hereinafter occasionally referred to as "ADH") into acetaldehyde ($CH_3CHO$). During the course of this oxidation reaction, hydrogen is produced.

The acetaldehyde generated from the ethanol is further degraded by the activity of acetaldehyde dehydrogenase (hereinafter occasionally referred to as "ALDH") to generate acetic acid. When the acetic acid is generated, hydrogen is produced. The generated acetic acid is then further degraded into carbon dioxide and water.

As described above, organisms have enzymes that catalyze the reaction to degrade alcohol and generate hydrogen. If the fuel cell uses an alcohol fuel, such enzymes may be utilized as catalysts to efficiently degrade the alcohol fuel and generate hydrogen. The anode 20 of the fuel cell in accordance with the embodiment of the present invention contains ADH and ALDH as catalyst particles.

FIG. 2 is a schematic diagram showing an enlarged view of the area II surrounded by the dotted line of FIG. 1. As shown in FIG. 2, the anode 20 is made of a carrying body for a catalytic electrode (hereinafter referred to as "catalyst carrying body") in which several types of particles are carried on a carrier 22 made of carbon or the like. The anode 20 is formed by mixing the catalyst carrying body with a solution in which an electrolyte membrane which is the same as the anion exchange membrane 10 has been dissolved (or plunged), and applying the resulting mixture to the surface of the anion exchange membrane 10.

Specifically, the carrier 22 carries a catalyst 24 and ADH 26 as a first particle and ALDH 28 as a second particle. The catalyst 24 and the ADH 26 both catalyze the degradation of ethanol to generate acetaldehyde and hydrogen. The ALDH 28 catalyzes the degradation of the generated acetaldehyde to generate hydrogen.

The catalyst 24, the ADH 26, and the ALDH 28 are carried on the same carrier 22. Carried on the same carrier 22, respective particles of the catalyst 24, the ADH 26, and the ALDH 28 may be provided in proximity to each other on the same catalyst carrying body or on adjacent catalyst carrying bodies. Therefore, the acetaldehyde produced by the degradation of ethanol due to the catalytic function of the catalyst 24 and the ADH 26 may be immediately degraded by the ALDH 28 provided in proximity to the catalyst 24 and the ADH 26. Thus, it is possible to increase the rate of the reaction to generate hydrogen from ethanol, and to rapidly produce a large amount of hydrogen.

Organisms have plural types of ADHs as enzymes that degrade alcohol. Specific examples of the ADHs include ADH1, ADH2, ADH3, ADH4, ADH5, ADH6, and ADH7. Any one or a plurality of these ADHs may be used as the first particle.

Organisms also have plural types of ALDHs as enzymes that degrade acetaldehyde. Specific examples of the ALDHs include ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH7A1P1, ALDH8A1, ALDH9A1, ALDH16A1, and ALDH18A1. Any one or a plurality of these ALDHs may be used as the second particle.

Figure 3:
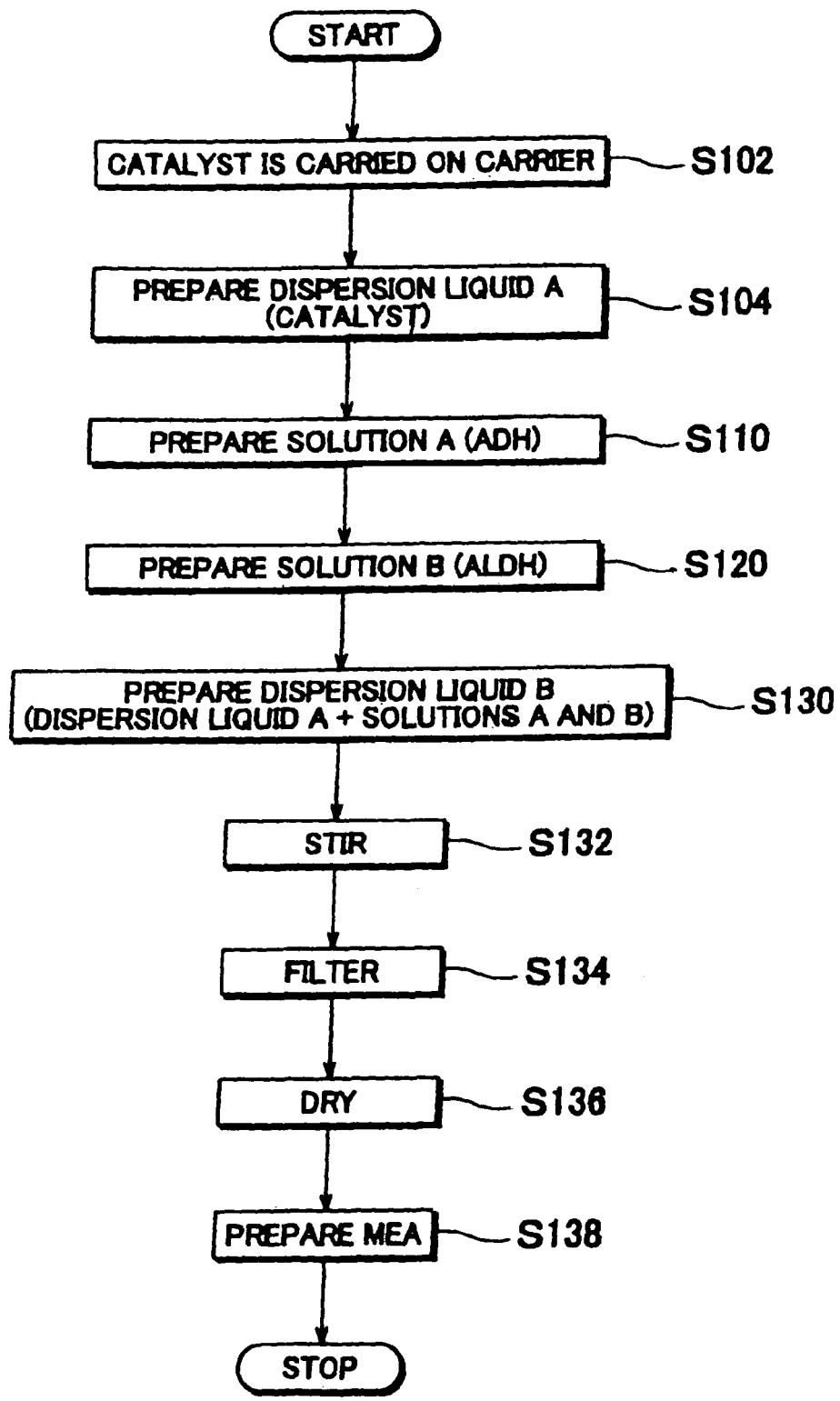
FIG. 3 is a flowchart showing a method for preparing the electrode catalyst of the fuel cell in accordance with the embodiment of the present invention.

FIG. 3 is a flowchart showing a method for preparing an anode in accordance with the embodiment of the present invention. In FIG. 3, first, a carrying body in which the catalyst 24 is carried on the carrier 22 is prepared (S102). Because the method for preparing such a carrying body is known, it is not specifically described here. Then, the carrying body prepared in step S102 is dispersed in a dispersion liquid to prepare a dispersion liquid A (S104).

Next, a solution A in which the ADH 26 is cultured is prepared (S110). Likewise, a solution B in which the ALDH 28 is cultured is prepared (S120). Because the method for culturing such enzymes is known, it is not specifically described here.

Then, the solution A containing ADH 26 and the solution B containing ALDH 28 are mixed to prepare a mixed solution (S130). The mixing ratio between the solution A and the solution B is determined so that the molar proportion between the ADH 26 and the ALDH 28 contained in the resulting mixed solution is in the range of 1:4 to 4:1, in other words, the ratio in the number of moles of ADH 26 to the number of moles of ALDH 28 is in the range of 0.25 to 4. Then, the mixed solution is mixed with the dispersion liquid A prepared in step S104 to prepare a dispersion liquid B (S132).

The dispersion liquid B prepared is stirred (S134). This causes the ADH 26 and the ALDH 28 to be carried on the carrier 22 carrying the catalyst 24. Then, the dispersion solution B is filtered to extract the carrier 22 on which the respective particles are carried. Thereafter, the extracted carrier is dried to prepare a catalyst (S138).

Thereafter, the catalyst is mixed with the electrolyte solution in which an electrolyte membrane composing an anion exchange membrane 10 has been dissolved, and the resulting mixture is applied to the anion exchange membrane 10. Consequently, an anode 20 having the carrier 22 carrying the catalyst 24, ADH 26, and ALDH 28 as a catalyst is formed on the surface of the anion exchange membrane 10. In order to avoid destruction of ADH 26 and ALDH 28 due to heat, all the processes in the above method involving ADH 26 or ALDH 28 (S110, S120, and S130 to S138) are performed at a temperature of 70° C. or less, more preferably 60° C. or less.

According to the embodiment described above, the catalyst 24, which is made of Pt—Ru or the like, ADH 26, and ALDH 28 are used as catalytic particles. This improves the fuel efficiency by efficiently breaking the C—C bond in ethanol in the fuel.

Figures 4, 5:
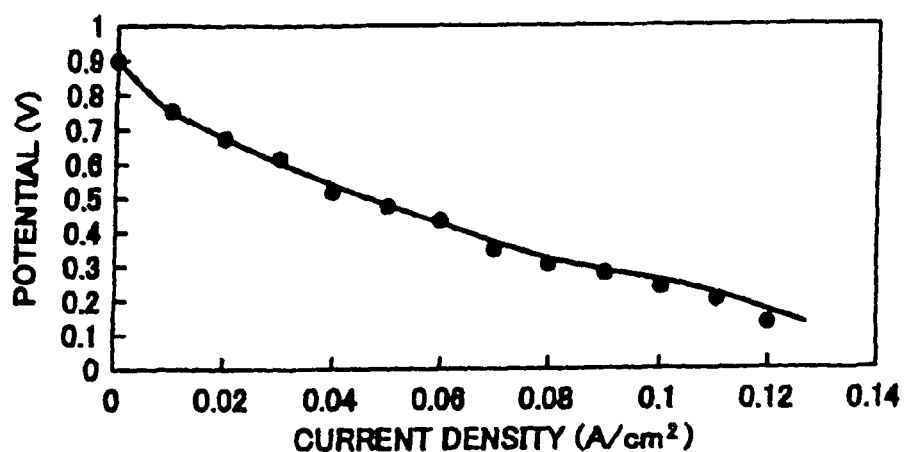
FIG. 4 is a chart showing the I-V characteristics of the fuel cell in accordance with the embodiment of the present invention.
FIG. 5 is a table showing changes in the current density with different proportions of alcohol dehydrogenase and acetaldehyde dehydrogenase contained in the catalyst of the fuel cell in accordance with the embodiment of the present invention.

FIG. 4 is a chart showing the I-V characteristics of the fuel cell manufactured as described above. In FIG. 4, the horizontal axis represents the current density [A/cm$^2$], and the vertical axis represents the voltage [V]. As can be seen from FIG. 4, the fuel cell in accordance with the embodiment has enhanced power generation performance achieving higher cell voltages over the entire range of current densities.

FIG. 5 is a table showing changes in the current density [A/cm$^2$] with different proportions of ADH 26 and ALDH 28 in the amount carried on the carrier 22 in accordance with the embodiment. In FIG. 5, ADH1 is used as the ADH 26, and ALDH2 is used as the ALDH 28. Pt—Ru is used as the catalyst 24. The proportion between Pt and Ru contained in the catalyst 24 is Pt/Ru=58 [wt %]. The proportion in the volume of Pt and Ru contained in the catalyst 24 is Pt:Ru=1:2.

As can be seen from FIG. 5, at a voltage of 0.6 [V], the current density is highest in the region where the molar proportion between ADH 26 and ALDH 28 in the amount carried on the carrier 22 is 40:60. The molar proportion between ADH 26 and ALDH 28 is not limited to 40:60, and may be different from that. Molar proportions in the range of 20:80 to 80:20, in other words, ratios in number of moles of ADH 26 to ALDH 28 in the range of 0.25 to 4, are particularly effective. Molar proportions in the range of 20:80 to 60:40, in other words, ratios in number of moles of ADH 26 to ALDH 28 in the range of 0.25 to 1.5, are further preferred.

Figure 6:
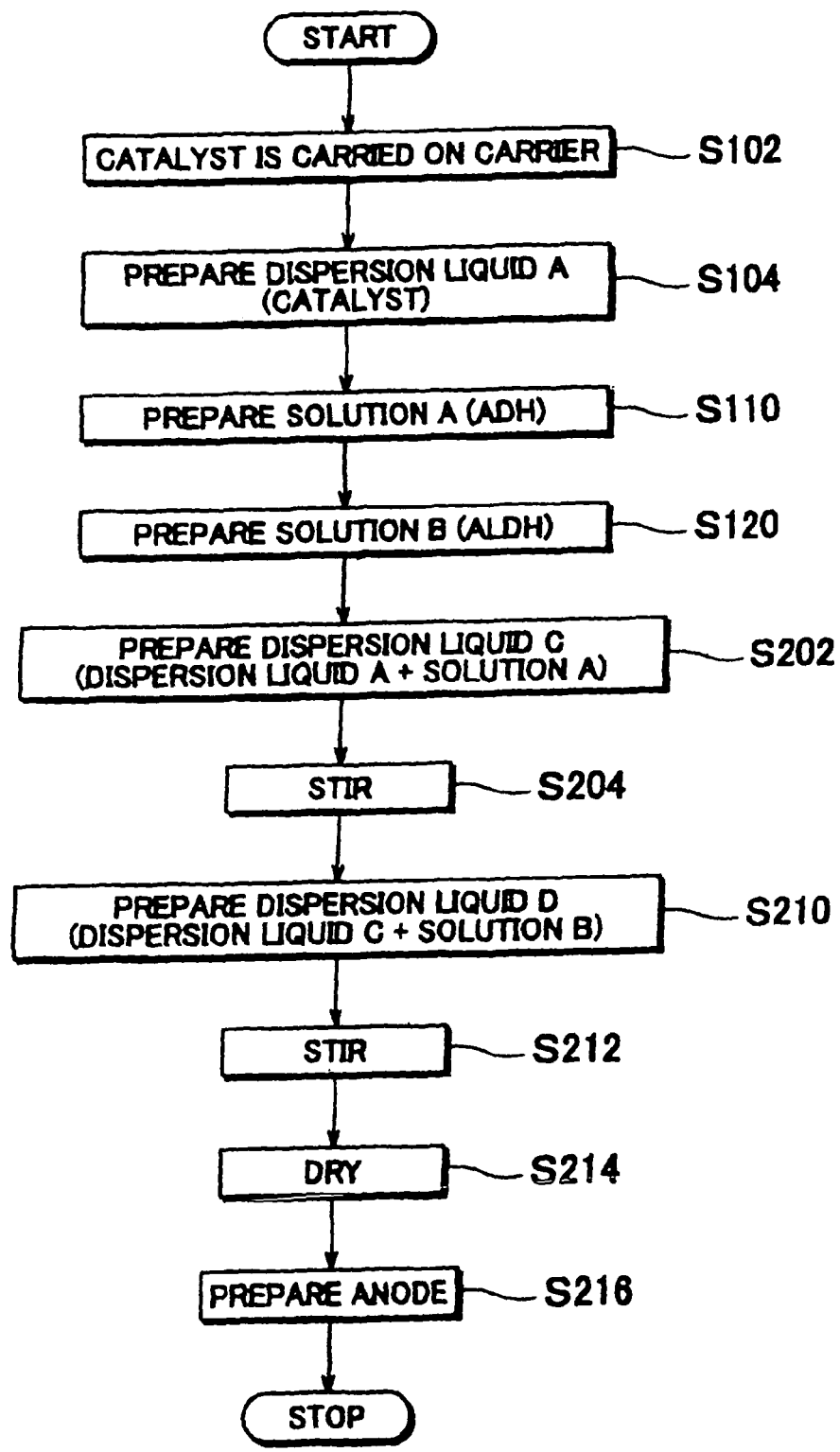
FIG. 6 is a flowchart showing another method for preparing the electrode catalyst of the fuel cell in accordance with the embodiment of the present invention.

The method for preparing catalytic particles in accordance with the present invention is not limited to that described above, and they may be prepared by other methods. FIG. 6 is a flowchart showing another method for preparing catalytic particles in accordance with the embodiment of the present invention.

In the preparation method of FIG. 6, dispersion liquid A, the solution A, and solution B are each prepared in the processes same as those of FIG. 3 (S102 to S104, S110, and S120), and thereafter dispersion liquid C is prepared by mixing dispersion liquid A with solution A (S202). Thereafter, the dispersion liquid C is stirred (S204). This causes the catalyst 24 and the ADH 26 to be carried on the carrier 22 in the dispersion liquid C. Further, in step S210, dispersion liquid D is prepared by mixing dispersion liquid C with solution B. Thereafter, the dispersion liquid D is stirred (S212). This causes the catalyst 24, the ADH 26, and the ALDH 28 to be carried on the carrier 22 in the dispersion liquid D. Thereafter, the same processes as those in S136 to S138 of FIG. 3 are performed to prepare the anode 20.

The preparation method is not limited to that of FIG. 6. For example, the order of mixing the solution A and mixing the solution B may be reversed. That is, the dispersion liquid A may be mixed with the solution B to prepare a dispersion liquid in steps S202 to S204, and after stirring the resulting dispersion liquid, it may be mixed with the solution A to prepare a catalyst carrying body in steps S210 to S212.

Also, in the above preparation method, for example, the preparation of the dispersion liquid A (S102 to S104), the preparation of the solution A (S110), and the preparation of the solution B (S120) may be performed in any order, as long as those dispersion liquid and solutions have been prepared before their mixing processes.

In the embodiment described above, three types of catalytic particles, namely the catalyst 24, the ADH 26, and the ALDH 28, are carried on a single carrier. However, the present invention is not limited thereto. Specifically, because the catalyst 24 and the ADH 26 both have a catalytic function of degrading mainly alcohol, either of the catalyst 24 and the ADH 26 may be used. Other catalyst or enzymes that catalyze the degradation of alcohol may also be used. For example, the ADH 26 may be replaced with microsomal ethanol oxidase (MEOS), which also is known as another enzyme that degrades alcohol.

Likewise, other enzymes having the same or similar activity as ALDH 28 or other particles that catalyze the degradation of acetaldehyde may also be used instead.

Moreover, enzymes that directly degrade alcohol into carbon dioxide and water such as cytochrome P450, for example, may be used as the first particle and the second particle. In this case, the catalyst 24 and cytochrome P450 are carried on the carrier 22, so that the cytochrome P450 degrades alcohol into acetaldehyde and further degrades the acetaldehyde to produce hydrogen. Thus, the same effect as that described above are achieved.

If cytochrome P450 is used, for example, the catalyst may be prepared as described below. In step S110 of FIG. 6, a solution in which cytochrome P450 is cultured is prepared as the solution A. The preparation of the solution B in step S120 is omitted. In subsequent steps S202 to S204, the dispersion liquid A and the solution A are mixed and stirred. Thereafter, without performing steps S210 to S212, the stirred mixture is directly subjected to processes of steps S214 to S216 to prepare the anode 20.

In the above description, Pt—Ru is used as the catalyst 24. However, the catalyst 24 in accordance with the present invention is not limited thereto, and may contain Fe, Co, Ni, Fe—Co—Ni, Pt, or Pt—Sn, for example.

In the embodiment described above, the structure of the cathode 30 is different from that of the anode 20. However, the present invention is not limited thereto, and the cathode 30 may have the same structure as that of the anode 20. The surfaces of the electrodes 20 and 30 may be covered by a diffusion layer composed of a porous material or the like.

Furthermore, in the embodiment in accordance with the present invention, the fuel cell has only one membrane-electrode assembly (MEA) in which a pair of electrodes (the anode 20 and the cathode 30) is disposed on opposite sides of the anion exchange membrane 10, and in which the current collecting plates 40 and the reaction gas paths 50 and 60 are disposed on one side of each respective electrode. However, the fuel cell in accordance with the present invention is not limited to the structure shown in FIG. 1, and may have a stack structure, for example, in which a plurality of MEAs are connected in series via a separator that includes a current collecting plate. Also in this case, by providing the anode 20 of each MEA with a catalyst carrying body carrying the catalyst 24, the ADH 26, and the ALDH 28 as described above, it is possible to streamline the fuel utilization in each MEA, and to improve the power generation performance of the entire fuel cell. In addition, the surfaces of the catalyst layers of the anode 20 and the cathode 30 each may be covered by a diffusion layer.

In the embodiment described above, the fuel cell is an alkali fuel cell using the anion exchange membrane 10. However, the present invention is not limited thereto, and the fuel cell may be an alkali fuel cell using an electrolyte that is permeable to negative ions such as KOH instead of the anion exchange membrane 10. In this case, it is possible to reduce deterioration of the electrolyte by reducing the permeability of the electrolyte to hydrogen peroxide ions. Although the electrode in accordance with the embodiment is advantageously applied to alkali fuel cells, the present invention is not limited to application to alkali fuel cells, and may be applied to solid polymer fuel cells, which use a proton exchange membrane as the electrolyte membrane, and so forth. Also in this case, by supplying the anode with a fuel containing alcohol and having a C—C bond the fuel utilization rate may be improved.

The number, quantity, amount, range, and so forth mentioned for each element in the above description of the embodiment serve as examples only and should not be construed as limitative. Also, the structures, the method steps, and so forth in the above description of the embodiment are illustrative only and should not be construed as essential to the present invention.

The invention claimed is:

1. A fuel cell that uses alcohol as fuel, comprising:
an electrolyte; and
an anode and a cathode disposed across the electrolyte, wherein:
the anode contains a first particle of alcohol dehydrogenase that catalyzes the degradation of alcohol, and a second particle of aldehyde dehydrogenase that catalyzes the degradation of aldehyde; and
the first particle contains at least one of Fe, Co, Ni, Fe—Co—Ni, Pt, Pt—Ru, and Pt—Sn.

2. The fuel cell according to claim 1, wherein the first particle contains Pt—Ru.

3. The fuel cell according to claim 1, wherein the second particle contains acetaldehyde dehydrogenase.

4. The fuel cell according to claim 1, wherein the first particle and the second particle both contain cytochrome P450.

5. The fuel cell according to claim 1, wherein:
the anode includes a carrying body in which the first particle and the second particle are both carried on the same carrier.

6. The fuel cell according to claim 1, wherein:
the second particle contains an acetaldehyde dehydrogenase; and
the molar ratio of the alcohol dehydrogenase to the acetaldehyde dehydrogenase is 0.25 to 4.

7. The fuel cell according to claim 6, wherein the molar ratio of the alcohol dehydrogenase to the acetaldehyde dehydrogenase is 0.25 to 1.5.

8. The fuel cell according to claim 1, wherein the electrolyte is an anion exchange membrane.

9. A method of manufacturing a fuel cell that uses alcohol as fuel and that has an anion exchange membrane as an electrolyte, the method comprising:
mixing a first solution that contains alcohol dehydrogenase and a second solution that contains acetaldehyde dehydrogenase;

drying mixed solution obtained by mixing the first solution and the second solution;

dissolving an anion exchange membrane in a solution to form an electrolyte solution;

mixing a dried substance obtained by drying the mixed solution with the electrolyte solution; and applying the electrolyte solution, mixed with the dried substance, to the anion exchange membrane.

10. The method according to claim 9, wherein the molar ratio of the alcohol dehydrogenase to the acetaldehyde dehydrogenase contained in the mixed solution is 0.25 to 4.

* * * * *